United States Patent [19]

Hallenbach et al.

[11] Patent Number: 5,374,605

[45] Date of Patent: Dec. 20, 1994

[54] ISOXAZOLECARBOXYLIC ACID DERIVATIVES

[75] Inventors: Werner Hallenbach, Monheim; Hans-Joachim Santel, Leverkusen; Klaus Lürssen; Robert R. Schmidt, both of Bergisch Gladbach, all of Germany

[73] Assignee: Bayer Aktiengesellschaft, Leverkusen, Germany

[21] Appl. No.: 2,307

[22] Filed: Jan. 8, 1993

[30] Foreign Application Priority Data

Jan. 17, 1992 [DE] Germany ............... 4201047

[51] Int. Cl.$^5$ ............... C07D 261/08; C07D 261/10; A01N 43/80
[52] U.S. Cl. ............... 504/252; 504/271; 546/275; 548/248
[58] Field of Search ............... 548/248; 504/271, 252; 546/275

[56] References Cited

FOREIGN PATENT DOCUMENTS

| 0418667 | 3/1991 | European Pat. Off. ............ 548/248 |
| 2459237 | 12/1979 | France ............... 548/248 |
| 2062373 | 12/1970 | Germany ............... 548/248 |

OTHER PUBLICATIONS

CA 109:190423e Preparation . . . fungicides. Suzuki et al., p. 716, 1988.
CA 114:43487d Preparation of . . . antimycotics. Schaller et al., p. 813, 1991.
CA 115:92250a Preparation of . . . herbicides. Maywald et al., p. 764, 1991.
Chemical Abstracts, vol. 72, No. 25, Jun. 22, 1970, Columbus, Ohio, US; abstract No. 132705e, pp. 365 & PS-A-7 007 054 (Fujisawa Pharmaceutical Co., Ltd), Mar. 11, 1970.

*Primary Examiner*—Johann Richter
*Assistant Examiner*—Joseph K. McKane
*Attorney, Agent, or Firm*—Sprung Horn Kramer & Woods

[57] ABSTRACT

The invention relates to isoxazolecarboxylic acid derivatives of the general formula (I)

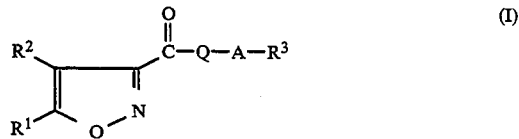

in which

A represents alkanediyl,

Q represents oxygen, sulphur, imino (NH) or alkylimino (N-alkyl), $R^1$ represents an in each case optionally substituted radical from the series comprising alkyl, cycloalkyl or phenyl, $R^2$ represents hydrogen, halogen or optionally substituted alkyl, and $R^3$ represents in each case optionally substituted cyclohexyl or phenyl, with the exception of the compounds: N-benzyl-5-cyclopropyl-isoxazole-3-carboxamide N-(2-phenylethyl)-5-methyl-isoxazole-3-carboxamide and N-benzyl-5-methyl-isoxazole-3-carboxamide, a process for their preparation, and their use as herbicides.

9 Claims, No Drawings

ISOXAZOLECARBOXYLIC ACID DERIVATIVES

The invention relates to new isoxazolecarboxylic acid derivatives, to a process for their preparation, and to their use as herbicides.

A series of isoxazolecarboxylic acid derivatives have already been disclosed as herbicides or as intermediates for herbicides (cf. EP-A 418,667). However, they were hitherto unimportant as herbicides.

Other isoxazolecarboxylic acid derivatives have been disclosed as pharmaceuticals or as intermediates for the preparation of pharmaceuticals (cf. DE-OS (German Published Specification) 2,950,380; JP-A 45,007,054—cited in Chem. Abstracts 72: 132705e).

New isoxazolecarboxylic acid derivatives of the general formula (I) have now been found,

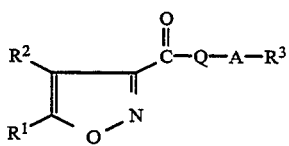

in which
A represents alkanediyl,
Q represents oxygen, sulphur, imino (NH) or alkylimino (N-alkyl),
$R^1$ represents an in each case optionally substituted radical from the series comprising alkyl, cycloalkyl or phenyl,
$R^2$ represents hydrogen, halogen or optionally substituted alkyl, and
$R^3$ represents in each case optionally substituted cyclohexyl, phenyl, pyridyl, furyl or thienyl,
the following, previously known compounds being excepted by disclaimer:
N-benzyl-5-cyclopropyl-isoxazole-3-carboxamide (cf. EP-A 418,667, p. 71), N-(2-phenyl-ethyl)-5-methyl-isoxazole-3-carboxamide (cf. DE-OS (German Published Specification) 2,950,380) and N-benzyl-5-methyl-isoxazole-3-carboxamide (cf. JP-A 45,007,054—cited in Chem. Abstracts 72: 132705e).

The new compounds of the formula (I) are obtained when isoxazolecarboxylic acid derivatives of the general formula (II)

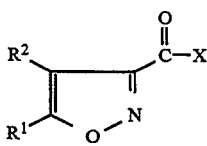

in which
X represents halogen or alkoxy and
$R^1$ and $R^2$ have the abovementioned meanings, are reacted with nucleophilic compounds of the general formula (III)

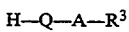 (III)

in which
A, Q and $R^3$ have the abovementioned meanings,
if appropriate in the presence of an acid acceptor and if appropriate in the presence of a diluent.

The new isoxazolecarboxylic acid derivatives of the general formula (I) are distinguished by a powerful herbicidal activity.

The invention preferably relates to compounds of the formula (I) in which
A represents $C_1$—$C_4$-alkanediyl,
Q represents oxygen, sulphur, imino (NH) or $C_1$—$C_4$-alkylimino,
$R^1$ represents a radical from the series comprising $C_1$—$C_6$-alkyl and $C_3$—$C_6$-cycloalkyl, each of which is optionally substituted by halogen or $C_1$—$C_4$-alkoxy, or represents phenyl which is optionally substituted by halogen or by $C_1$—$C_4$-alkyl or $C_1$—$C_4$-alkoxy (each of these being optionally substituted by halogen),
$R^2$ represents hydrogen, halogen or optionally halogen-substituted $C_1$—$C_{10}$-alkyl and
$R^3$ represents cyclohexyl, phenyl, pyridyl, furyl or thienyl, each of which is optionally substituted by nitro, cyano, carboxy, halogen or by $C_1$—$C_4$-alkyl, $C_1$—$C_4$alkoxy, $C_1$—$C_4$-alkylthio, $C_1$—$C_4$-alkylsulphinyl or $C_1$—$C_4$-alkylsulphonyl (each of these being optionally substituted by halogen),
the compounds N-benzyl-5-cyclopropyl-isoxazole-3-carboxamide, N-(2-phenyl-ethyl)-5-methyl-isoxazole-3-carboxamide and N-benzyl-5-methyl-isoxazole-3-carboxamide being excepted by disclaimer.

The hydrocarbon groups mentioned in the definition of the compounds according to the invention, such as alkyl or alkanediyl, are in each case straight-chain or branched, also in compounds with hetero atoms, such as in alkoxy.

In particular, the invention relates to compounds of the formula (I) in which
A represents methylene (—$CH_2$—), ethane-1,2-diyl (dimethylene, —$CH_2CH_2$—),

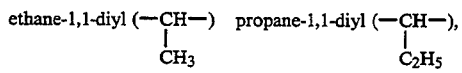

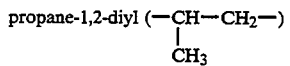

or propane-1,3-diyl (—$CH_2CH_2CH_2$—),
Q represents oxygen, imino (NH) or methylimino ($NCH_3$),
$R^1$ represents a radical from the series comprising methyl, ethyl, propyl, isopropyl, butyl, isobutyl, sec-butyl or tert-butyl, each of which is optionally substituted by fluorine, chlorine, methoxy or ethoxy, or represents cyclopropyl, cyclobutyl, cyclopentyl or cyclohexyl, each of which is optionally substituted by fluorine, chlorine, methyl or ethyl, or represents phenyl which is optionally substituted by fluorine, chlorine, methyl or methoxy,
$R^2$ represents hydrogen, chlorine or methyl and
$R^3$ represents cyclohexyl, phenyl, pyridyl, furyl or thienyl, each of which is optionally substituted by nitro, cyano, carboxy, fluorine, chlorine, methyl, ethyl, trifluoromethyl, methoxy, ethoxy, difluoromethoxy or trifluoromethoxy,
with the exception of the compounds excepted by disclaimer.

If, for example, 5-methyl-isoxazole-3-carboxylic acid chloride and 1-phenyl-ethylamine are used as starting substances, the course of the reaction in the process according to the invention can be outlined by the following equation:

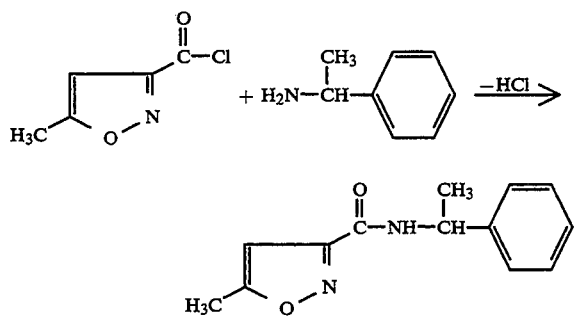

Formula (II) provides a general definition of the isoxazolecarboxylic acid derivatives to be used as starting substances in the process according to the invention for the preparation of compounds of the formula (I).

In formula (II), $R^1$ and $R^2$ preferably, or in particular, have those meanings which have already been mentioned above in connection with the description of the compounds of the formula (I) according to the invention as being preferred, or particularly preferred, for $R^1$ and $R^2$;

X preferably represents chlorine, methoxy or ethoxy.

The starting substances of the formula (II) are known and/or can be prepared by processes known per se (cf. JP-A 49,000,187—cited in Chem. Abstracts 81: 49671f; German Patent 1,670,952; U.S. Pat. No. 4,189,581; DE-OS (German Published Specification) 2,950,380; J. Heterocycl. Chem. 19 (1982), 557–560; Tetrahedron 43 (1987) 235–242; EP-A 418,667; Preparation Examples).

Formula (III) provides a general definition of the nucleophilic compounds furthermore to be used as starting substances in the process according to the invention for the preparation of compounds of the formula (I).

In formula (III), A, Q and $R^3$ preferably, or in particular, have those meanings which have already been mentioned above in connection with the description of the compounds of the formula (I) according to the invention as being preferred, or particularly preferred, for A, Q and $R^3$.

The starting substances of the formula (III) are known chemicals for organic synthesis.

The process according to the invention for the preparation of the new compounds of the formula (I) is preferably carried out using diluents. Suitable diluents are all inert organic solvents. These preferably include aliphatic and aromatic, optionally halogenated hydrocarbons such as pentane, hexane, heptane, cyclohexane, petroleum ether, benzine, ligroine, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, nitriles such as, for example, acetonitrile and propionitrile, amides such as, for example, dimethylformamide, dimethylacetamide and N-methyl-pyrrolidone, and also dimethyl sulphoxide, tetramethylene sulphone and hexamethylphosphoric triamide.

Acid acceptors which can be employed in the process according to the invention are all acid-binding agents which can customarily be used for reactions of this type. The following are preferably suitable: alkali metal hydrides and alkaline earth metal hydrides such as lithium hydride, sodium hydride, potassium hydride and calcium hydride, alkali metal hydroxides and alkaline earth metal hydroxides such as lithium hydroxide, sodium hydroxide, potassium hydroxide and calcium hydroxide, alkali metal carbonates, alkali metal hydrogen carbonates, alkaline earth metal carbonates and alkaline earth metal hydrogen carbonates such as sodium carbonate, potassium carbonate or sodium hydrogen carbonate and potassium hydrogen carbonate, as well as calcium carbonate, alkali metal acetates such as sodium acetate and potassium acetate, alkali metal alcoholates such as sodium methylate, sodium ethylate, sodium propylate, sodium isopropylate, sodium butylate, sodium isobutylate, sodium tert-butylate, potassium methylate, potassium ethylate, potassium propylate, potassium isopropylate, potassium butylate, potassium isobutylate and potassium tert-butylate, furthermore basic nitrogen compounds such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

When carrying out the process according to the invention, the reaction temperatures can be varied within a substantial range. In general, the process is carried out at temperatures between 0° C. and 150° C., preferably at temperatures between 10° C. and 100° C.

The process according to the invention is generally carried out under atmospheric pressure. However, it is also possible to carry out the process under increased or reduced pressure.

For carrying out the process according to the invention, the starting substances required in each case are generally employed in approximately equimolar amounts. However, it is also possible to use one of the two components employed in each case in a larger excess. The reactions are generally carried out in a suitable diluent in the presence of an acid acceptor, and the reaction mixture is stirred for several hours at the temperature required in each case. Working-up in the process according to the invention is carried out in each case by customary methods (cf. the Preparation Examples).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The compounds of the formula (I) according to the invention are particularly suitable for selectively combating monocotyledon and dicotyledon weeds in monocotyledon and dicotyledon cultures, both by the pre- and the postemergence methods.

The active compounds can be converted into the customary formulations, such as solutions, emulsions, wettable powders, suspensions, powders, dusting agents, pastes, soluble powders, granules, suspension-emulsion concentrates, natural and synthetic substances impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 5 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known hericides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxy-phenoxyalkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 10 g and 10 kg of active compound per hectare of soil surface, preferably between 50 g and 5 kg per ha.

The preparation and use of the active compounds according to the invention can be seen from the following examples.

PREPARATION EXAMPLES

EXAMPLE 1

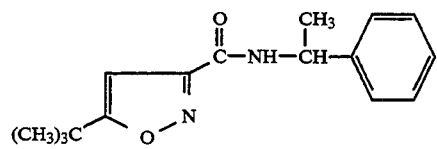

A solution of 6.0 g (32 mmol) of 5-tert-butyl-isoxazole-3-carboxylic acid chloride in 10 ml of chloroform is added dropwise at 20° C. with stirring to a mixture of 3.9 g (32 mmol) of 1-phenyl-ethylamine, 5.5 ml (39.5 mmol) of triethylamine and 40 ml of chloroform. The reaction mixture is stirred for 15 hours at 20° C. and then poured into approximately the same volume of water, and the batch is shaken thoroughly. The organic phase is separated off, washed with 2 N hydrochloric acid and then with saturated sodium hydrogen carbonate solution, dried with sodium sulphate and filtered. The solvent is carefully removed from the filtrate by distillation under a water pump vacuum. After degassing in an oil pump vacuum, the reaction product remains as a solid residue.

7.9 g (91% of theory) of (R/S)-N-(1-phenyl-ethyl)-5-tert-butyl-isoxazole-3-carboxamide of melting point 88° C. are obtained.

Other compounds of the formula (I) which can be prepared analogously to Example 1 and following the general description of the preparation process according to the invention are also, for example, those listed in Table 1 below.

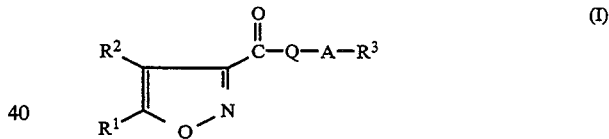

TABLE 1

Examples of the compounds of the formula (I)

| Ex. No. | A | Q | R¹ | R² | R³ | Melting point (°C.) |
|---|---|---|---|---|---|---|
| 2 | (R/S)—CH— \| CH₃ | NH | C(CH₃)₃ | H | ⌬-OCH₃ (2-methoxyphenyl) | 134 |
| 3 | (S)—CH— \| CH₃ | NH | C(CH₃)₃ | H | phenyl | 92 |
| 4 | (R/S)—CHCH₂CH₂— \| CH₃ | NH | C(CH₃)₃ | H | phenyl | 70 |
| 5 | (R)—CH— \| CH₃ | NH | C(CH₃)₃ | H | cyclohexyl | 93 |

TABLE 1-continued

Examples of the compounds of the formula (I)

| Ex. No. | A | Q | R¹ | R² | R³ | Melting point (°C.) |
|---|---|---|---|---|---|---|
| 6 | (R/S)—CH(CH₃)— | NH | C(CH₃)₃ | H | 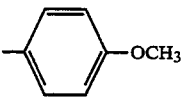 4-OCH₃-C₆H₄- | 92 |
| 7 | —CH₂CH₂— | NH | C(CH₃)₃ | H |  C₆H₅- | 93 |
| 8 | (R)—CH(CH₃)— | NH | C(CH₃)₃ | H |  C₆H₅- | 91 |
| 9 | —CH₂— | O | C(CH₃)₃ | H | 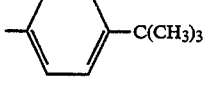 4-C(CH₃)₃-C₆H₄- | 53 |
| 10 | —CH₂CH₂— | O | C(CH₃)₃ | H |  C₆H₅- | (Oil) |
| 11 | (R/S)—CH(CH₃)— | NH | C(CH₃)₃ | H | 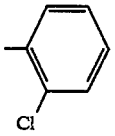 2-Cl-C₆H₄- | 128 |
| 12 | (R/S)—CH(CH₃)— | NH | C(CH₃)₃ | H | 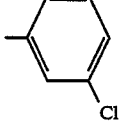 3-Cl-C₆H₄- | 114 |
| 13 | (R/S)—CH(CH₃)— | NH | C(CH₃)₃ | H | 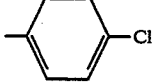 4-Cl-C₆H₄- | 137 |
| 14 | —CH₂— | NH | C(CH₃)₃ | H | 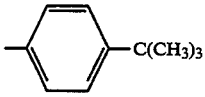 4-C(CH₃)₃-C₆H₄- | 97 |
| 15 | (R/S)—CH(CH₃)— | NH | C(CH₃)₃ | H | 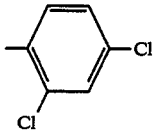 2,4-Cl₂-C₆H₃- | 126 |
| 16 | (R/S)—CH(CH₃)— | NH | C(CH₃)₃ | H | 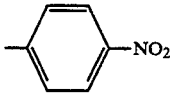 4-NO₂-C₆H₄- | 107 |
| 17 | (R/S)—CH(CH₃)— | NH | C(CH₃)₃ | H |  4-F-C₆H₄- | 135 |

TABLE 1-continued
Examples of the compounds of the formula (I)
| Ex. No. | A | Q | R¹ | R² | R³ | Melting point (°C.) |
|---|---|---|---|---|---|---|
| 18 | (S)—CH—<br>\|<br>CH₃ | NH | C(CH₃)₃ | H | 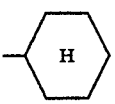 | 97 |
| 19 | —CH₂— | NH | C(CH₃)₃ | H | 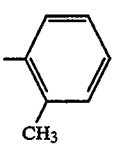 | 74 |
| 20 | —CH₂— | NH | C(CH₃)₃ | H | 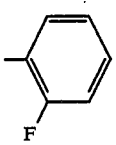 | 107 |
| 21 | —CH₂— | NH | C(CH₃)₃ | H | 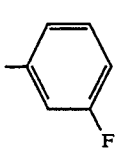 | 81 |
| 22 | —CH₂— | NH | C(CH₃)₃ | H | 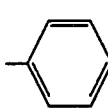 | 87 |
| 23 | —CH₂— | NH | C(CH₃)₃ | H | 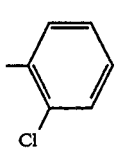 | 107 |
| 24 | —CH₂— | NH | C(CH₃)₃ | H | 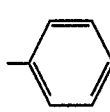 | 127 |
| 25 | —CH₂— | NH | C(CH₃)₃ | H | 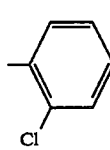 | 115 |
| 26 | —CH₂— | NH | C(CH₃)₃ | H | 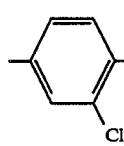 | 114 |
| 27 | —CH₂— | NH | C(CH₃)₃ | H | 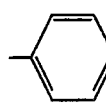 | (amorph) |
| 28 | —CH₂— | NH | C(CH₃)₃ | H | 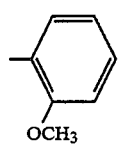 | (amorph) |

TABLE 1-continued

Examples of the compounds of the formula (I)

| Ex. No. | A | Q | R¹ | R² | R³ | Melting point (°C.) |
|---|---|---|---|---|---|---|
| 29 | —CH₂— | NH | C(CH₃)₃ | H | 3,4-dimethoxyphenyl (—OCH₃, —OCH₃) | 94 |
| 30 | —CH₂— | NH | C(CH₃)₃ | H | 2-ethoxyphenyl (—OC₂H₅) | 64 |
| 31 | (R/S)—CH(CH₃)— | NH | 2,6-dichlorophenyl (Cl, Cl) | H | phenyl | (amorph) |
| 32 | (R/S)—CH(CH₃)— | NH | 2,6-difluoro... (F, Cl) | H | phenyl | 124 |
| 33 | —CH₂— | NH | 2-F, 6-Cl phenyl | H | 4-tert-butylphenyl (—C(CH₃)₃) | 115 |
| 34 | (R/S)—CH(CH₃)— | NCH₃ | 2-F, 6-Cl phenyl | H | phenyl | (amorph) |
| 35 | (R/S)—CH(CH₃)— | NCH₃ | 2-F, 6-Cl phenyl | H | 4-chlorophenyl (—Cl) | (amorph) |
| 36 | —CH₂— | O | 2-F, 6-Cl phenyl | H | 4-tert-butylphenyl (—C(CH₃)₃) | 56 |
| 37 | —CH₂— | NH | C(CH₃)₃ | H | 3-trifluoromethylphenyl (—CF₃) | 83 |

TABLE 1-continued

Examples of the compounds of the formula (I)

| Ex. No. | A | Q | R¹ | R² | R³ | Melting point (°C.) |
|---|---|---|---|---|---|---|
| 38 | —CH₂— | NH | C(CH₃)₃ | H | 4-CF₃-C₆H₄ | 119 |
| 39 | —CH₂— | NH | C(CH₃)₃ | H | 2-CF₃-C₆H₄ | 89 |
| 40 | —CH₂— | NH | C(CH₃)₃ | H | 3-CH₃-C₆H₄ | 82 |
| 41 | —CH₂— | NH | C(CH₃)₃ | H | 4-CH₃-C₆H₄ | 111 |
| 42 | —CH₂— | NH | C(CH₃)₃ | H | 2,4-F₂-C₆H₃ | 99 |
| 43 | —CH₂— | NH | C(CH₃)₃ | H | 2,5-F₂-C₆H₃ | 110 |
| 44 | —CH₂— | NH | C(CH₃)₃ | H | 3,5-(CF₃)₂-C₆H₃ | 118 |
| 45 | —CH₂— | NH | C(CH₃)₃ | H | 2,6-F₂-C₆H₃ | 97 |
| 46 | —CH₂— | NH | C(CH₃)₃ | H | 4-COOH-C₆H₄ | 187 |
| 47 | —CH₂— | NH | C(CH₃)₃ | H | 3,4-F₂-C₆H₃ | 79 |

TABLE 1-continued
Examples of the compounds of the formula (I)
| Ex. No. | A | Q | R¹ | R² | R³ | Melting point (°C.) |
|---|---|---|---|---|---|---|
| 48 | —CH₂— | NH | C(CH₃)₃ | H | 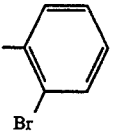 | 96 |
| 49 | —CH₂— | NH | C(CH₃)₃ | H | 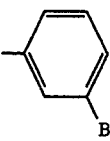 | 62 |
| 50 | —CH₂— | NH | C(CH₃)₃ | H | 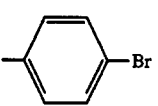 | 136 |
| 51 | —CH₂— | NH | C(CH₃)₃ | H | 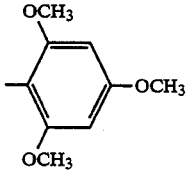 | 121 |
| 52 | —CH₂— | NH | C(CH₃)₃ | H | 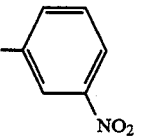 | 94 |
| 53 | —CH₂— | NH | C(CH₃)₃ | H | 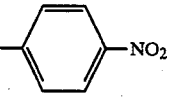 | 120 |
| 54 | (R/S)—CH—<br>　　　\|<br>　　　CH₃ | NH | CH₃ | H | 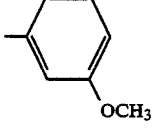 | |
| 55 | (R/S)—CH—<br>　　　\|<br>　　　CH₃ | NH | CH₂CH(CH₃)₂ | H | 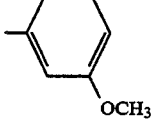 | |
| 56 | (R/S)—CH—<br>　　　\|<br>　　　CH₃ | NH | CH(CH₃)₂ | H | 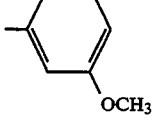 | |
| 57 | (R/S)—CH—<br>　　　\|<br>　　　CH₃ | NH | CH₃ | H | 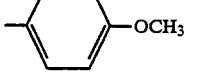 | |

TABLE 1-continued

Examples of the compounds of the formula (I)

| Ex. No. | A | Q | R¹ | R² | R³ | Melting point (°C.) |
|---|---|---|---|---|---|---|
| 58 | (R/S)—CH—CH₃ | NH | CH₂CH(CH₃)₂ | H | 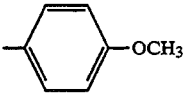 4-OCH₃-phenyl | |
| 59 | (R/S)—CH—CH₃ | NH | CH(CH₃)₂ | H | 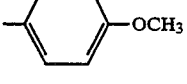 4-OCH₃-phenyl | |
| 60 | (R/S)—CH—CH₃ | NH | CH₃ | H | 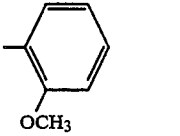 2-OCH₃-phenyl | |
| 61 | (R/S)—CH—CH₃ | NH | CH₂CH(CH₃)₂ | H | 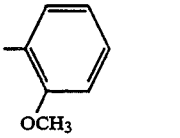 2-OCH₃-phenyl | |
| 62 | (R/S)—CH—CH₃ | NH | CH(CH₃)₂ | H | 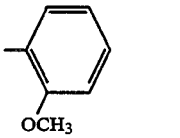 2-OCH₃-phenyl | |
| 63 | (R/S)—CH—CH₃ | NH | CH₃ | H | 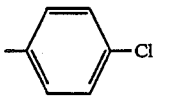 4-Cl-phenyl | |
| 64 | (R/S)—CH—CH₃ | NH | CH₂CH(CH₃)₂ | H | 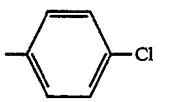 4-Cl-phenyl | |
| 65 | (R/S)—CH—CH₃ | NH | CH(CH₃)₂ | H | 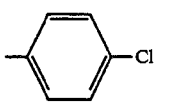 4-Cl-phenyl | |
| 66 | (R/S)—CHCH₂CH₂—CH₃ | NH | CH₂CH(CH₃)₂ | H | 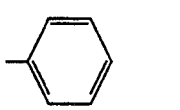 phenyl | |
| 67 | (R/S)—CH—CH₃ | NH | CH₂CH(CH₃)₂ | H | 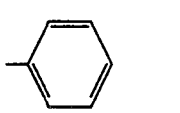 phenyl | |
| 68 | (R/S)—CHCH₂CH₂—CH₃ | NH | CH(CH₃)₂ | H | 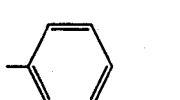 phenyl | |
| 69 | (R/S)—CH—CH₃ | NH | CH(CH₃)₂ | H | 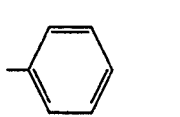 phenyl | |

TABLE 1-continued

Examples of the compounds of the formula (I)

| Ex. No. | A | Q | R¹ | R² | R³ | Melting point (°C.) |
|---|---|---|---|---|---|---|
| 70 | (R/S)—CH(CH₃)— | NH | CH₃ | H | 3-Cl-C₆H₄ | |
| 71 | (R/S)—CH(CH₃)— | NH | CH₂CH(CH₃)₂ | H | 3-Cl-C₆H₄ | |
| 72 | (R/S)—CH(CH₃)— | NH | CH(CH₃)₂ | H | 3-Cl-C₆H₄ | |
| 73 | (R/S)—CH(CH₃)— | NH | CH₃ | H | 2-Cl-C₆H₄ | |
| 74 | (R/S)—CH(CH₃)— | NH | CH₂CH(CH₃)₂ | H | 2-Cl-C₆H₄ | |
| 75 | (R/S)—CH(CH₃)— | NH | CH(CH₃)₂ | H | 2-Cl-C₆H₄ | |
| 76 | (R/S)—CH(CH₃)— | NH | C(CH₃)₃ | H | 3-CH₃-C₆H₄ | |
| 77 | (R/S)—CH(CH₃)— | NH | C(CH₃)₃ | H | 2-F-C₆H₄ | |
| 78 | (R/S)—CH(CH₃)— | NH | CH(CH₃)₂ | H | 3-CH₃-C₆H₄ | |
| 79 | (R/S)—CH(CH₃)— | NH | CH₂CH(CH₃)₂ | H | 3-CH₃-C₆H₄ | |

TABLE 1-continued
Examples of the compounds of the formula (I)
| Ex. No. | A | Q | R$^1$ | R$^2$ | R$^3$ | Melting point (°C.) |
|---|---|---|---|---|---|---|
| 80 | (R/S)—CH—<br>\|<br>CH$_3$ | NH | CH$_2$CH(CH$_3$)$_2$ | H | 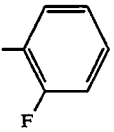 | |
| 81 | —CH$_2$— | NH | CH$_2$CH(CH$_3$)$_2$ | H | 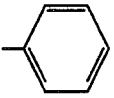 | |
| 82 | (R/S)—CH—<br>\|<br>CH$_3$ | NH | CH$_3$ | H | 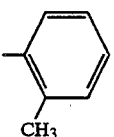 | |
| 83 | (R/S)—CH—<br>\|<br>CH$_3$ | NH | CH$_3$ | H | 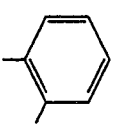 | |
| 84 | —CH$_2$— | NH | CH$_3$ | H | 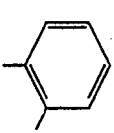 | 84 |
| 85 | —CH$_2$— | NH | CH$_3$ | H | 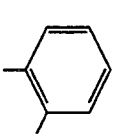 | 102 |
| 86 | —CH$_2$— | NH | CH$_3$ | H | 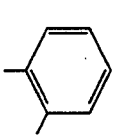 | 95 |
| 87 | —CH$_2$— | NH | CH$_3$ | H | 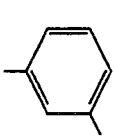 | 79 |
| 88 | —CH$_2$— | NH | CH$_3$ | H | 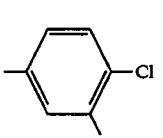 | 136 |
| 89 | —CH$_2$— | NH | CH$_3$ | H | 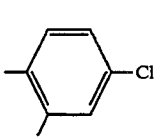 | 143 |

TABLE 1-continued

Examples of the compounds of the formula (I)

| Ex. No. | A | Q | R$^1$ | R$^2$ | R$^3$ | Melting point (°C.) |
|---|---|---|---|---|---|---|
| 90 | —CH$_2$— | NH | CH$_3$ | H | 4-OCH$_3$-C$_6$H$_4$ | 89 |
| 91 | —CH$_2$— | NH | CH$_3$ | H | 2-OCH$_3$-C$_6$H$_4$ | — |
| 92 | —CH$_2$— | NH | CH$_3$ | H | 3-CH$_3$-C$_6$H$_4$ | 64 |
| 93 | —CH$_2$— | NH | CH$_3$ | H | 4-F-C$_6$H$_4$ | 118 |
| 94 | —CH$_2$— | NH | CH$_3$ | H | 3-CF$_3$-C$_6$H$_4$ | 81 |
| 95 | —CH$_2$— | NH | CH$_3$ | H | 4-Cl-C$_6$H$_4$ | 143 |
| 96 | —CH$_2$— | NH | CH$_3$ | H | 4-OCH$_3$-C$_6$H$_4$ | 109 |
| 97 | —CH$_2$— | NH | CH$_3$ | H | 2,6-di-F-C$_6$H$_3$ | 125 |
| 98 | —CH$_2$— | NH | CH$_3$ | H | 4-CH$_3$-C$_6$H$_4$ | 89 |
| 99 | —CH$_2$— | NH | CH$_3$ | H | 3,4-di-OCH$_3$-C$_6$H$_3$ | 115 |
| 100 | —CH$_2$— | NH | CH$_3$ | H | 2,5-di-F-C$_6$H$_3$ | 128 |

TABLE 1-continued
Examples of the compounds of the formula (I)
| Ex. No. | A | Q | R¹ | R² | R³ | Melting point (°C.) |
|---|---|---|---|---|---|---|
| 101 | —CH₂— | NH | CH₃ | H | 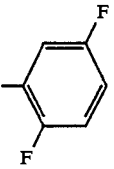 2,5-F₂-phenyl | 106 |
| 102 | —CH₂— | NH | CH₃ | H | 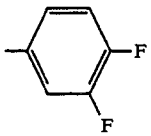 3,4-F₂-phenyl | 115 |
| 103 | —CH₂— | NH | CH₃ | H | 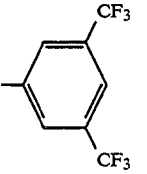 3,5-(CF₃)₂-phenyl | 101 |
| 104 | —CH₂— | NH | CH₃ | H | 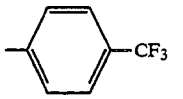 4-CF₃-phenyl | 146 |
| 105 | —CH₂— | NH | CH₃ | H | 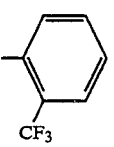 3-CF₃-phenyl | 113 |
| 106 | —CH₂— | NH | CH₃ | H | 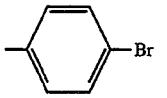 4-Br-phenyl | 137 |
| 107 | —CH₂— | NH | CH(CH₃)₂ | H | 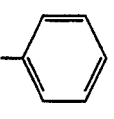 phenyl | |
| 108 | —CH₂— | NH | CH(CH₃)₂ | H | 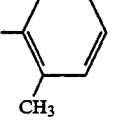 3-CH₃-phenyl | |
| 109 | —CH₂— | NH | CH₂CH(CH₃)₂ | H | 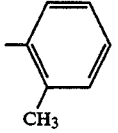 3-CH₃-phenyl | |
| 110 | —CH₂— | NH | CH₂CH(CH₃)₂ | H | 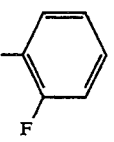 3-F-phenyl | |

TABLE 1-continued
Examples of the compounds of the formula (I)
| Ex. No. | A | Q | R¹ | R² | R³ | Melting point (°C.) |
|---|---|---|---|---|---|---|
| 111 | —CH₂— | NH | CH₂CH(CH₃)₂ | H | 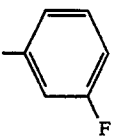 3-F-phenyl | |
| 112 | —CH₂— | NH | CH₂CH(CH₃)₂ | H | 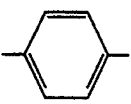 4-F-phenyl | |
| 113 | —CH₂— | NH | CH(CH₃)₂ | H | 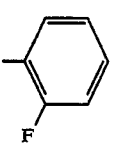 2-F-phenyl | |
| 114 | —CH₂— | NH | CH(CH₃)₂ | H | 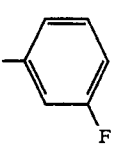 3-F-phenyl | |
| 115 | —CH₂— | NH | CH(CH₃)₂ | H | 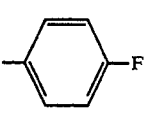 4-F-phenyl | |
| 116 | —CH₂— | NH | C(CH₃)₃ | H | 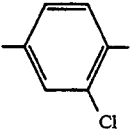 3-Cl-4-F-phenyl | 113 |
| 117 | —CH₂— | NH | C(CH₃)₃ | H | 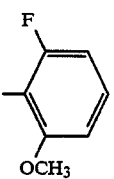 2-F-3-OCH₃-phenyl | 67 |
| 118 | —CH₂— | NH | C(CH₃)₃ | H | 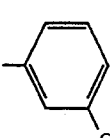 3-Cl-phenyl | 54 |
| 119 | —CH₂— | NH | C(CH₃)₃ | H | 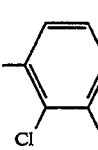 2,3-diCl-phenyl | 129 |
| 120 | —CH₂— | NH | C(CH₃)₃ | H | 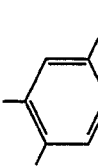 2,5-diCl-phenyl | 127 |

TABLE 1-continued

Examples of the compounds of the formula (I)

| Ex. No. | A | Q | R¹ | R² | R³ | Melting point (°C.) |
|---|---|---|---|---|---|---|
| 121 | —CH$_2$— | NH | C(CH$_3$)$_3$ | H | 2,5-dichlorophenyl | 131 |
| 122 | —CH$_2$— | NH | C(CH$_3$)$_3$ | H | 2,3-dimethylphenyl | 60 |
| 123 | —CH$_2$— | NH | C(CH$_3$)$_3$ | H | 2,3-dimethoxyphenyl | 77 |
| 124 | —CH$_2$— | NH | C(CH$_3$)$_3$ | H | 2-chloro-3-methylphenyl | 119 |
| 125 | —CH$_2$— | NH | C(CH$_3$)$_3$ | H | 3,5-dimethoxyphenyl | 84 |
| 126 | —CH$_2$— | NH | C(CH$_3$)$_3$ | H | 2,6-dimethoxyphenyl | 116 |
| 127 | —CH$_2$— | NH | C(CH$_3$)$_3$ | H | 2,4-dichloro-6-methylphenyl | 109 |
| 128 | —CH$_2$— | NH | C(CH$_3$)$_3$ | H | pyridin-2-yl | — |
| 129 | —CH$_2$— | NH | C(CH$_3$)$_3$ | H | pyridin-3-yl | 89 |
| 130 | —CH$_2$— | NH | C(CH$_3$)$_3$ | H | pyridin-4-yl | 64 |

TABLE 1-continued

Examples of the compounds of the formula (I)

| Ex. No. | A | Q | R¹ | R² | R³ | Melting point (°C.) |
|---|---|---|---|---|---|---|
| 131 | (R/S)—CH—<br>\|<br>CH₃ | NH | C(CH₃)₃ | H | 2-pyridyl | |
| 132 | —CH₂— | NH | C(CH₃)₃ | H | 2-thienyl | 81 |
| 133 | (R/S)—CH—<br>\|<br>C₂H₅ | NH | C(CH₃)₃ | H | phenyl | 106 |
| 134 | —CH₂— | NH | C(CH₃)₃ | H | 2-furyl | 59 |
| 135 | (R/S)—CH—<br>\|<br>CH₃ | NH | C(CH₃)₃ | H | 2-furyl | |
| 136 | (R/S)—CH—<br>\|<br>CH₃ | NH | C(CH₃)₃ | H | 2-thienyl | 50 |
| 137 | —CH₂— | NH | C(CH₃)₃ | H | 3-OCF₃-phenyl | 67 |
| 138 | —CH₂— | NH | C(CH₃)₃ | H | 4-OCF₃-phenyl | 103 |
| 139 | —CH₂— | NH | C(CH₃)₃ | H | 3-F,5-CF₃-phenyl | 82 |

Starting Substances of the Formula (II)

EXAMPLE (II-1)

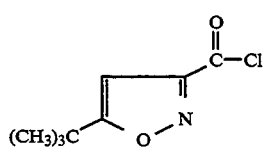

A mixture of 28.7 g (0.17 mol) of 5-tert-butyl-isoxazole-3-carboxylic acid and 70 ml of thionyl chloride is refluxed for 3 hours and then worked up by distillation.

19 g (60 % of theory) of 5-tert-butyl-isoxazole-3-carboxylic acid chloride of boiling point 60° C. (at 0.5 mbar) are obtained.

Use Examples:

EXAMPLE A

Post-Emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0%=no action (like untreated control)
100%=total destruction

In this test, a powerful action against weeds combined with a good compatibility with crop plants such as, for example, wheat, is shown for example by the compounds in accordance with Preparation Examples 1 and 3.

EXAMPLE B

Pre-Emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, a powerful action against weeds combined with good compatibility with crop plants such as, for example, maize and cotton, is shown for example by the compound of Preparation Example 1.

It will be understood that the specification and examples are illustrative but not limitative of the present invention and that other embodiments within the spirit and scope of the invention will suggest themselves to those skilled in the art.

What is claimed is:

1. An isoxazolecarboxylic acid derivative of the general formula (I)

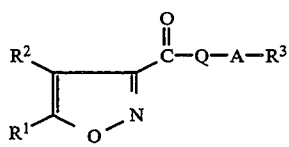

wherein
A represents methylene, ethane-1,1-diyl, propane-1,1-diyl, propane-1,2-diyl or propane-1,3-diyl,
Q represents oxygen, imino or methylimino,
$R^1$ represents a radical from the group consisting of methyl, ethyl, propyl, isopropyl, butyl, isobutyl, sec-butyl or tert-butyl, each of which is optionally substituted by fluorine, chlorine, methoxy or ethoxy, or represents cyclopropyl, cyclobutyl, cyclopentyl or cyclohexyl, each of which is optionally substituted by fluorine, chlorine, methyl or ethyl, $R^2$ represents hydrogen, chlorine or methyl and
$R^3$ represents cyclohexyl, phenyl, pyridyl, furyl or thienyl, each of which is optionally substituted by nitro, cyano, carboxy, fluorine, chlorine, methyl, ethyl, trifluoromethyl, methoxy, ethoxy, difluoromethoxy or trifluoromethoxy,
provided that $R^3$ cannot be unsubstituted phenyl or phenyl substituted with methyl or ethyl when $R^1$ is methyl or ethyl, and with the exception of the compounds N-benzyl-5-cyclopropyl-isoxazole-3-carboxamide, N-(2-phenyl-ethyl)-5-methyl-isoxazole-3-carboxamide and N-benzyl-5-methyl-isoxazole-3-carboxamide.

2. A compound according to claim 1 wherein such compound is (R/S)-N-((1-phenylethyl)-5-tert.-butyl-isoxazole-3-carboxamide of the formula

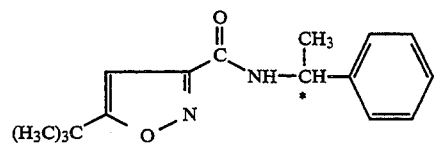

3. A compound according to claim 1 wherein such compound is (S)-N-(1-phenylethyl)-5-tert.-butyl-isoxazole-3-carboxamide of the formula

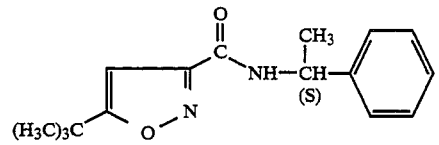

4. A compound according to claim 1 wherein such compound is (R)-N-(1-phenylethyl)-5-tert.-butyl-isoxazole-3-carboxamide of the formula

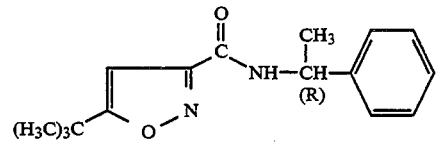

5. A compound according to claim 1 wherein such compound is (R/S)-N-(1-(2-chlorophenyl)ethyl-5-tert.-butyl-isoxazole-3-carboxamide of the formula

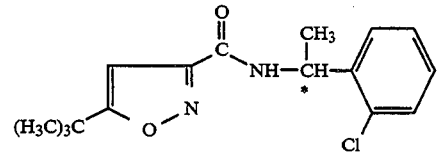

6. A compound according to claim 1 wherein such compound is N-(2,5-difluorophenyl)methyl-5-methyl-isoxazole-3-carboxamide of the formula

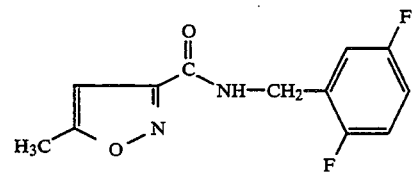

7. A herbicidal composition comprising a herbicidally effective amount of a compound according to claim 1 and a diluent.

8. A method of combating unwanted vegetation which comprises applying to such vegetation or to a locus from which it is desired to exclude such vegetation or herbicidally effective amount of a compound according to claim 1.

9. The method according to claim 8, wherein such compound is (R/S)-N-(1-phenylethyl)-5-tert.-butyl-isoxazole-3-carboxamide, (S)-N-(1-phenylethyl)-5-tert.-butyl-isoxazole-3-carboxamide, (R)-N-(1-phenylethyl)-5-tert.-butyl-isoxazole-3-carboxamide, (R/S)-N-(1-(2-chlorophenyl)ethyl)-5-tert.-butyl-isoxazole-3-carboxamide, (N-(2,5-difluorophenyl)methyl-5-methyl-isoxazole-3-carboxamide.

* * * * *